(12) United States Patent
Wang et al.

(10) Patent No.: US 8,796,281 B2
(45) Date of Patent: Aug. 5, 2014

(54) LIGHTING DEVICE HAVING AT LEAST ONE HEAT SINK

(75) Inventors: Yuqiang Wang, Guangdong (CN); Yewei Sun, Guangdong (CN); Pei Yu, Guangdong (CN); Jing Du, Guangdong (CN); Gaoxiao Zhang, Guangdong (CN)

(73) Assignee: Jinan University (CN)

( * ) Notice: Subject to any disclaimer, the term of this patent is extended or adjusted under 35 U.S.C. 154(b) by 51 days.

(21) Appl. No.: 13/254,653

(22) PCT Filed: Jul. 1, 2011

(86) PCT No.: PCT/CN2011/076756
§ 371 (c)(1),
(2), (4) Date: Jan. 23, 2012

(87) PCT Pub. No.: WO2012/003784
PCT Pub. Date: Jan. 12, 2012

(65) Prior Publication Data
US 2012/0115874 A1    May 10, 2012

(30) Foreign Application Priority Data
Jul. 5, 2010  (CN) .......................... 2010 1 0217332

(51) Int. Cl.
*A61K 31/4965* (2006.01)
*C07D 241/26* (2006.01)

(52) U.S. Cl.
USPC ..................................... 514/255.06; 544/336

(58) Field of Classification Search
CPC .................................................. C07D 241/26
USPC ........................................................ 544/336
See application file for complete search history.

(56) References Cited

U.S. PATENT DOCUMENTS

| | | |
|---|---|---|
| 2004/0106620 A1 | 6/2004 | Yoon et al. |
| 2009/0082356 A1 | 3/2009 | Gaillard et al. |
| 2011/0034485 A1 | 2/2011 | Wang et al. |

FOREIGN PATENT DOCUMENTS

| | | |
|---|---|---|
| CN | 101296909 A | 10/2008 |
| CN | 101468970 A | 7/2009 |
| WO | WO-2010/031789 A1 | 3/2010 |

OTHER PUBLICATIONS

Edamatsu, R., et al., "The Spin-Trap N-*Tert*-α-Phenyl-Butylnitrone Prolongs the life Span of the Senescence Accelerated Mouse", *Biochemical and Biophysical Research Communications*, 211(3), (1995), 847-849.

Kornfeld, R. A., et al., "Formation of Alkyl Heteroaromatics in the Pyrolysis of Pyrazylethanoi and Pyridylethanol Derivatives", *J. Argric. Food Chem.* 30., (1982), 668-672.

Sack, C. A., et al., "Antioxidant treatment with phenyl-α-*tert*-butyl nitrone (PBN) improves the cognitive performance and survival of aging rats", *Neuroscience Letters*, 205, (1996), 181-184.

*Primary Examiner* — Brian McDowell
(74) *Attorney, Agent, or Firm* — Schwegman, Lundberg & Woessner, P.A.

(57) ABSTRACT

The present invention provides pyrazine derivatives of formula I

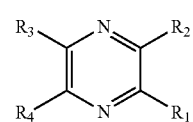

and pharmaceutically acceptable salts thereof, wherein the designation of $R_1$, $R_2$, $R_3$ and $R_4$ is provided herein. The invention also provides syntheses for preparation of such compounds. The invention further provides methods of use of these compounds and pharmaceutical compositions containing them for treatment and/or prevention of diseases and for manufacture of medicaments. These compounds and pharmaceutical compositions have antioxidative and thrombolytic effects, and thus can be used for the treatment and/or prevention of cerebral stroke caused by ischemia, and used for manufacture of medicaments for the treatment and/or prevention of nervous system diseases caused by excessive amount of radicals and/or thrombosis, infectious diseases, metabolic system diseases, cardiovascular and cerebrovascular diseases, and age-related degenerative diseases.

5 Claims, 2 Drawing Sheets

US 8,796,281 B2

LIGHTING DEVICE HAVING AT LEAST ONE HEAT SINK

CROSS-REFERENCE TO RELATED APPLICATIONS

This application is a nationalization under 35 U.S.C. §371 of International Application No. PCT/CN2011/076756, filed on Jul. 1, 2011 and published as WO 2012/003784 A1, on Jan. 12, 2012, which claims priority under 35 U.S.C. §119 to Chinese Application No. 201010217332.7, filed Jul. 5, 2010, the entire contents of which are incorporated herein by reference in their entirety.

FIELD OF THE INVENTION

The present invention relates to pyrazine derivatives and processes for preparation thereof and uses thereof in the manufacture of medicaments for treating and preventing diseases of the nervous system caused by excessive production of radicals and/or thrombosis, cardiovascular and cerebrovascular diseases, age-related degenerative diseases, and metabolic diseases.

BACKGROUND OF THE INVENTION

Oxygen is an essential element for the lives of human beings and animals. In the regular processes of metabolism, the human body produces different kinds of Reactive Oxygen Species (ROS), and also possesses many ways to inactivate ROS. Under normal conditions, the rate of ROS production will not exceed that of consumption via metabolism by tissues. However, in certain circumstances (for example, due to radiation, environmental factors, and overload of ferric ions), ROS may increase to a level exceeding that under the regulation of normal metabolism, or when something went wrong (e.g., caused by genetic defects) in the protective biological mechanism, the excessive amount of ROS may cause damage to cells and tissues, and thus induces some diseases and even causes death. Proteins, lipids and DNAs are substrates to which ROS may attack. In a human body, there are about $10^{12}$ oxygen molecules entering into the cells every day, $1/100$ of which destroy proteins, and $1/200$ of which destroy DNAs. Especially when the human body's capacity of natural resistance is low, ROS may become very harmful due to such destructions on DNAs, proteins and lipids.

In a regular condition, the anti-radical defense system of the human body is effective against the harm to the body caused by the radicals. In a pathological condition, however, some of the damaging radicals may escape from elimination, and these escaped radicals and their products may act directly upon cellular DNA, proteins and lipids, causing some damages on DNA and inducing overoxidation of cell membrane lipids. These results caused by ROS are called oxidative stress, and the oxidative stress can influence regular gene expression, cell differentiation and necrocytosis. Today, oxidative stress is considered a factor causing many diseases.

Formation of cerebral atherosclerosis and thromboembolus may induce cerebral stroke. In the developed countries, the cerebrovascular diseases have been shown as the third leading cause for human death following heart diseases and tumors, and 5% of the elderly people over 65 years old suffer from cerebral stroke. In the United States, for example, more than 500,000 people are reported suffering from severe stroke, where 70-85% of the cerebral stroke is related to ischemic stroke, which has a mortality rate of 15-33%. The methods currently used for treatment of acute ischemic stroke include cytoprotection and thrombolysis, while cytoprotection is used to prevent cell death during ischemic reperfusion, and thrombolysis is used mainly to keep blood vessels clear using thrombolytic drugs during an early period of the disease. Despite much of the efforts, the cerebral stroke is still one of the most devastating diseases for medical treatments. One of the reasons that the current treatments for cerebral stroke are far from satisfactory is that so far no drugs have clearly demonstrated both thrombolytic and cytoprotective effects.

Parkinson's disease (PD) is a disease with clinical manifestations of resting tremor, myotonia, hypokinesia, and abnormal gait posture. It is currently known that the primary pathologic change of PD is of substantia nigra-striatum, which decreases the production of dopamine, and causes the above-mentioned clinical manifestations. The causes of substantia nigra degeneration are still unclear. Currently, most of the related studies suggested that oxidative stress plays an important role in the pathologic progress of PD.

Researchers found that many chemical substances show some radical-eliminating effects. Nitrones are a type of the compounds having a strong antioxidative activity and in vivo biological activity. The final products formed from the reactions of nitrones and radicals include hydroxylamine derivatives, aldehydes, amines, and nitroxide radicals.

Phenyl-tert-Butyl Nitrones (PBN) can react with radicals to form nitroxide radicals, while nitroxide radicals are able to directly react with and thus eliminate other radicals, and also are able to oxidize reductive metals so as to inhibit the Fenton reduction and the metal-catalyzed Haber-Weiss reaction. When aging accelerated mice were intraperitoneally injected with PBN daily, an increase of 33% in the lifespan of the mice was indicated (Edamatsu et al., Biochem. Biophys. Res. Commun. 211:847, 1995). When 24-month-old rats were intraperitoneally injected with 32 mg/kg of PBN daily for 9.5 months, it is indicated that lipid peroxidation reactions are diminished in two areas (cerebral cortex and globus pallidus) which are important for the cognitive function of the rats' brains, and at the same time, the cognitive ability for older rats is enhanced. More importantly, when the experiment was run for 32 months, 7 of the 11 rats injected with PBN were still alive (Sack et al., Neurosci. Lett. 205:181, 1996). Unfortunately, however, PBN is still merely applied in research and has not yet been developed into any drugs.

Tetramethylpyrazine (TMP, Chuxiongqin) is an active ingredient extracted from ligusticum wallichii (Chuanxiong), a traditional Chinese medicine. TMP has effects of radical elimination and thrombolysis/anticoagulation. TMP have been used clinically to treat cardiovascular and cerebrovascular diseases. It is founded that, however, the antioxidative effect of TMP is rather weak and its bioavailability is low. Clinically, multiple doses are needed for TMP to reach to an effective concentration.

Currently, there is no any effective curing method for the treatment of stroke, and the limited kinds of commercially available drugs are far from satisfactory due to inferior curative effects or toxic side effects. To be effective for any drugs to treat ischemic stroke, the following two functions are critical: thrombolysis and/or neuronal protection.

SUMMARY OF THE INVENTION

The present invention is directed to pyrazine derivatives and pharmaceutically acceptable salts thereof. These compounds and pharmaceutical compositions containing them showed strong effects of radical elimination and anticoagulation/thrombolysis, and strong capacity for neuroprotection.

The present invention is also directed to syntheses for preparation of the pyrazine derivatives and pharmaceutical compositions thereof.

The present invention is further directed to methods of use of the pyrazine derivatives and pharmaceutical compositions thereof for treatment of diseases and for manufacture of medicaments.

In one aspect of the invention, the pyrazine derivatives of the present invention are selected from compounds of formula I:

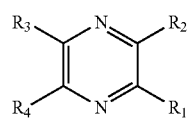

I or pharmaceutically acceptable salts thereof, wherein:

$R_1$ and $R_2$ are each independently hydrogen, hydroxyl, or a substituted or unsubstituted group selected from amino, carboxyl, alkyl, alkoxy, aryl, heteroaryl, esters, amines, carbamic acid ester and nitrones;

$R_3$ and $R_4$ are each independently hydrogen, hydroxyl, or a substituted or unsubstituted group selected from amino, carboxyl, alkyl, alkoxy, aryl, heteroaryl, esters, amines, carbamic acid ester, and nitrones; or $R_3$ and $R_4$ taken together with the carbon atom(s) they are attached form a substituted or unsubstituted fused ring.

$R_1$, $R_2$, $R_3$ and $R_4$ are not simultaneously hydrogen or methyl group;

If only one of $R_1$, $R_2$, $R_3$ and $R_4$ is a nitrone group, the nitrone group is not substituted by tertiary butyl.

According to some embodiments of the present invention, the compounds of formula I can be in a dimeric or polymeric structure through substitution of $R_1$ and/or $R_4$.

In addition, the pyrazine derivative and pharmaceutically acceptable salts thereof provided in the invention can form a pharmaceutical composition, which includes a pyrazine derivative as a pharmaceutically active ingredient in a therapeutically effective amount, and a pharmaceutically acceptable carrier and excipient.

In another aspect of the invention, the methods for preparing the pyrazine derivatives include the steps of, for example, oxidizing a starting compound of pyrazine to form an aldehyde using active selenium dioxide, and refluxing the resulting aldehyde with a hydroxylamine to product a pyrazine derivative with mono-substitution or multi-substitution of nitrone group. The method of preparation may also include the steps of reacting the starting pyrazine compound via bromination with NBS, and reacting with an active compound to produce a pyrazine composition.

In yet another aspect of the invention, the pyrazine derivatives can be used for treatment or prevention of the diseases induced by excessive production of ROS or thrombopoiesis and can be used to manufacture medicaments for the treatment or prevention of such diseases.

In comparison of the existing technologies, the present invention has the following advantages: The compounds of the present invention are novel in their structures and possess dual functions of thrombolysis and cytoprotection, and are capable of getting through blood-brain barrier, and further are safe and effective. These compounds are valuable candidates for new drugs for treating and/or preventing nervous system diseases caused by excessive radical production and/or thrombosis, infectious diseases, metabolic system diseases, cardiovascular and cerebrovascular diseases, age-related degenerative diseases, and cancers.

DETAILED DESCRIPTION OF THE EMBODIMENTS

Definitions

Figure 1:
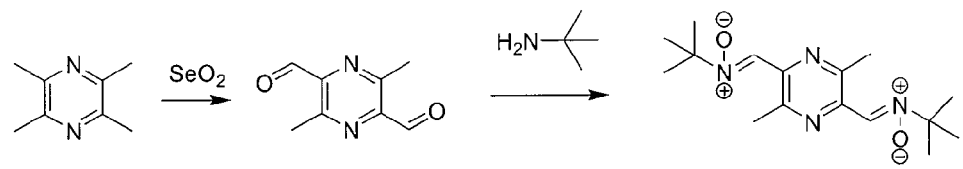
FIG. 1 illustrates a synthetic process for the compound TN-2 according to an embodiment of the present invention.

When describing the pyrazine derivatives and uses thereof, unless stated otherwise, the following terms and phrases as used herein are intended to have the following meanings.

As used herein, the term "alkyl" refers to an unsubstituted or substituted straight-chain, branched-chain, or cyclic-chain having up to 15 carbon atoms; the straight-alkyl includes, for example, methyl, ethyl, n-propyl, n-butyl, n-pentyl, n-hexyl, n-heptyl and n-octyl, the cyclic alkyl ("cycloalkyl") includes, for example, cyclopropyl, cyclobutyl, cyclopentyl and cyclohexyl, and further the alkyl can be substituted by one or more substituents which include but not limited to $NH_2$, $NO_2$, $N(CH_3)_2$, $ONO_2$, F, Cl, Br, I, OH, $OCH_3$, $CO_2H$, $CO_2CH_3$, CN, aryl, and hetroaryl. The term "alkyl" may also refer to an unsubstituted or substituted straight-chain, branched-chain, or cyclic alkyl having up to 15 carbon atoms, which further contains in the chain at least one heteroatom (e.g., nitrogen, oxygen, or sulfur); the above straight-chain alkyl includes, for example, $CH_2CH_2OCH_3$, $CH_2CH_2N(CH_3)_2$ and $CH_2CH_2SCH_3$; the branched-chain alkyl includes, for example, $CH_2CH(OCH_3)CH_3$, $CH_2CH(N(CH_3)_2)CH_3$ and $CH_2CH(OCH_3)CH_3$, the cyclic alkyl includes, for example, $CH(CH_2CH_2)_2O$, $H(CH_2CH_2)_2NCH_3$ and $CH(CH_2CH_2)_2S$, and further the alkyl can be substituted by one or more substituents which include but not limited to $NH_2$, $NO_2$, $N(CH_3)_2$, $ONO_2$, F, Cl, Br, I, OH, $OCH_3$, $CO_2H$, $CO_2CH_3$, CN, aryl, and heteroaryl.

As used herein, the term "aryl" refers to an unsubstituted or substituted aromatic group, carbocyclic group and heteroaryl. The aryl can be either a monocyclic group or a fused polycyclic group; for example, phenyl is a monocyclic aryl, and naphtyl is a fused polycyclic aryl. The aryl can be substituted by one or more substituents, which include but not limited to $NH_2$, $NO_2$, $N(CH_3)_2$, $ONO_2$, F, Cl, Br, I, OH, $OCH_3$, $CO_2H$, $CO_2CH_3$, CN, aryl, and heteroaryl.

The heteroaryl relates to substituted or an unsubstituted monocyclic or polycyclic group, where the ring contains at least one heteroatom, such as nitrogen, oxygen and sulfur. For example, a typical heteroaryl includes one or more nitrogen atoms such as in tetrazolyl, pyrrolyl, pyridyl (e.g., pyrid-4-yl, pyrid-3-yl, pyrid-2-yl), pyridazinyl, indyl, quinolyl (e.g., quinol-2-yl, quinol-3-yl), imidazolyl, isoquinolyl, pyrazolyl, pyrazinyl, pyrimidinyl, pyridonyl and pyridazinyl; a typical hetroaryl includes at least one oxygen atom such as in fur-2-yl, fur-3-yl and benzofuryl; a typical hetroaryl includes at least one surfur atom such as in thienyl and benzothienyl; a typical heteroaryl containing more than one kind of heteroatoms includes furoazetidinyl, oxazolyl, isoxazolyl, thiazolyl and phenothioxinyl. The heteroaryl can be substituted by one or more substituents which include but not limited to $NH_2$, $NO_2$, O-alkyl, NH-alkyl, N(alkyl)$_2$, NHC(O)-alkyl, $ONO_2$, F, Cl, Br, I, OH, $OCF_3$, $OSO_2CH_3$, $CO_2H$, $CO_2$-alkyl, CN, aryl, and polyaryl. Furthermore, the heteroaryl also includes those with a heteroatom in the ring being oxidized, for example, to form N-oxide, ketone, or sulfone.

The phrase "pharmaceutically acceptable," as used herein, means that there is no unacceptable toxicity in a salt or excipient. The pharmaceutically acceptable salts include inorganic anions such as those of chloride, bromide, iodide, sulfate, sulfite, nitrate, nitrite, and phosphate and phosphite, and organic anions such as those of acetate, propionate, cinnamate, tosylate, citrate, lactate and gluconate. In adding to the pharmaceutically acceptable excipients described herebelow, see also: E. W. Martin, in Remington's Pharmaceutical Sciences Mack Publishing Company (1995), Philadelphia, Pa., 19$^{th}$ ed.

Compounds, Preparation, Usage and Dosage

In one aspect, the present invention provides pyrazine derivatives of formula I:

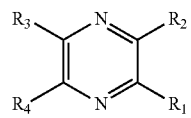

I and pharmaceutically acceptable salts thereof, wherein:

$R_1$ and $R_2$ are each independently hydrogen, hydroxyl, or a substituted or unsubstituted group selected from amino, carboxyl, alkyl, alkoxy, aryl, heteroaryl, esters, amines, carbamic acid ester, and nitrone;

$R_3$ and $R_4$ are each independently hydrogen, hydroxyl, or a substituted or unsubstituted group selected from amino, carboxyl, alkyl, alkoxy, aryl, heteroaryl, esters, amines, carbamic acid ester, and nitrone group; or $R_3$ and $R_4$ taken together with the carbon atom(s) they are attached form a substituted or unsubstituted fused ring.

$R_1$, $R_2$, $R_3$ and $R_4$ are not simultaneously hydrogen or methyl group;

If only one of $R_1$, $R_2$, $R_3$ and $R_4$ is a nitrone group, the nitrone group is not substituted by tertiary butyl.

In some embodiments, $R_1$ and $R_3$ in formula I are each independently a substituted or unsubstituted nitrone group, $R_2$ and $R_4$ are alkyls, and the pyrazine derivatives have a structure of formula II:

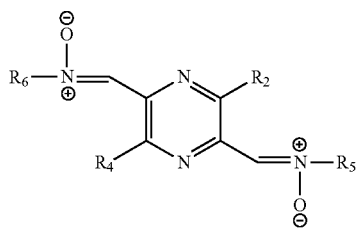

II wherein, $R_5$ and $R_6$ are each independently a substituted or unsubstituted straight-chain alkyl, branched-chain alkyl, or cycloalkyl.

In a preferred exemplary embodiment, $R_2$ and $R_4$ in formula II are methyl, and $R_5$ and $R_6$ are tert-butyl. Thus, the pyrazine derivative has a structure of TN-2 as follows:

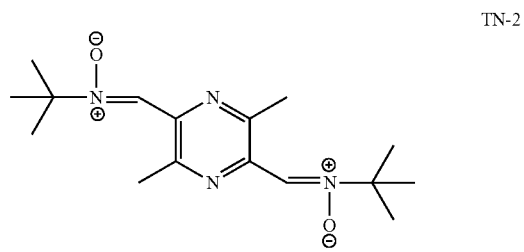 [SMILES: Cc1nc(/C=[N+](/[O-])C(C)(C)C)c(C)nc1/C=[N+](/[O-])C(C)(C)C]

TN-2

In another preferred exemplary embodiment, $R_2$ and $R_4$ in formula II are methyl, and $R_5$ and $R_6$ are cyclohexyl. Thus, the pyrazine derivative has a structure of TN-3 as follows:

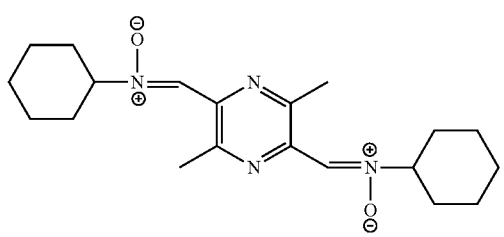

TN-3

In addition, in different embodiments of the compounds of formula I, $R_3$ and $R_4$ taken together with the carbon atom(s) they are attached form a substituted fused ring, while the substitute on the ring can be an alkyl, or one or more of nitrate groups. In some exemplary embodiments, the pyrazine derivatives have a structure of TN-4 or TN-5 as follows:

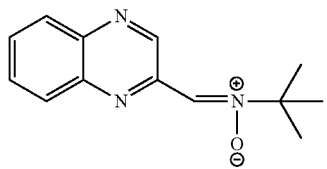

TN-4

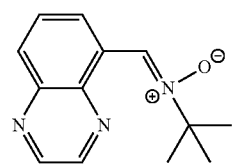

TN-5

In other embodiments, the pyrazine derivatives of formula I have a dimeric structure of formula III, or even a polymeric structure, through substitution on $R_9$ and/or $R_4$:

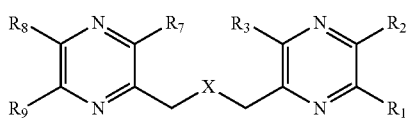

III wherein, $R_7$, $R_8$ and $R_9$ are each independently hydrogen, or a substituted or unsubstituted group of hydroxyl, alkyl, or nitrone group; X is C, O, N or S, attached to an adjacent carbon atom to form a hydrocarbon, ether, ammonia or sulfhydryl, or attached to an adjacent carbon atom that can be optionally further oxidized into carbonyl, to form a ketone, acyloxy, or acylamino.

In some embodiments, the pyrazine derivatives have the above-described dimeric structure, wherein X is N-tBu for example, and thus have a structure of formula IV:

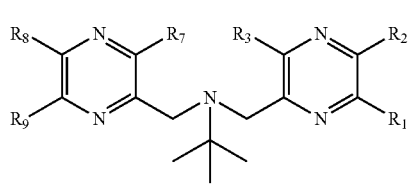

IV

Further, the pyrazine derivatives, having the dimeric structure of formula IV, can be selected from at least one of the compounds of TN-6 through TN-14 as follows:
TN-6: $R_1$, $R_2$, $R_3$, $R_7$, $R_8$, $R_9$=$CH_3$;
TN-7: $R_1$=HC=$N^+$(O-)tBu, $R_2$, $R_3$, $R_7$, $R_8$, $R_9$=$CH_3$;
TN-8: $R_1$, $R_9$=HC=$N^+$(O-)tBu, $R_2$, $R_3$, $R_7$, $R_8$=$CH_3$;
TN-9: $R_1$, $R_8$=HC=$N^+$(O-)tBu, $R_2$, $R_3$, $R_7$, $R_9$=$CH_3$;
TN-10: $R_1$, $R_3$, $R_8$=HC=$N^+$(O-)tBu, $R_2$, $R_7$, $R_9$=$CH_3$;
TN-11: $R_1$, $R_7$, $R_8$=HC=$N^+$(O-)tBu, $R_2$, $R_3$, $R_9$=$CH_3$;
TN-12: $R_1$, $R_2$, $R_7$, $R_8$=HC=$N^+$(O-)tBu, $R_3$, $R_9$=$CH_3$;
TN-13: $R_1$, $R_2$, $R_7$, $R_8$=HC=$N^+$(O-)tBu, $R_3$, $R_9$=$CH_3$;
TN-14: $R_1$, $R_2$, $R_3$, $R_7$, $R_8$, $R_9$=HC=$N^+$(O-)tBu$_o$ In addition, in exemplary embodiments, the pyrazine derivatives with the dimeric structure of formula IV can be TN-15 or TN-16 as follows:

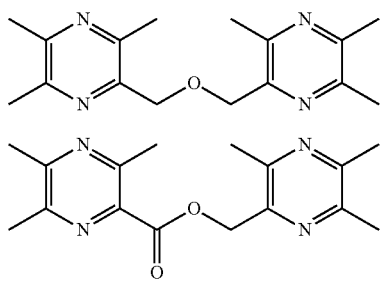

Further, in some other embodiments, the pyrazine derivatives of formula I can have a structure of formula V:

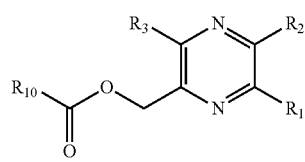

V wherein, $R_{10}$ is a substituted or unsubstituted straight-chain alkyl, branched-chain alkyl, cycloalkyl, or biologically active small molecule moiety including, lipoate or cysteine for example.

Furthermore, a pharmaceutical composition can be formed from the pyrazine derivative or pharmaceutically acceptable salts thereof. The pharmaceutical composition may include the pyrazine derivative, as a pharmaceutical active ingredient in a therapeutically effective amount, and a pharmaceutically acceptable carrier and excipient.

In the other aspect, methods of preparation of the pyrazine derivatives as described herein are provided in the invention. The methods, for example, can include the steps of oxidizing a starting compound of pyrazine into an aldehyde using active selenium dioxide, and refluxing the resulting aldehyde with an appropriate hydroxylamine for 3 hours to give a pyrazine derivative with a mono-substituted or multi-substituted nitrone.

In some other embodiments, a method of preparation of the pyrazine derivative includes the steps of reacting a starting compound of pyrazine via bromination with NBS, and further reacting with an active compound to form a pyrazine composition. Wherein, the active compound can be selected from, for example, the following ones:

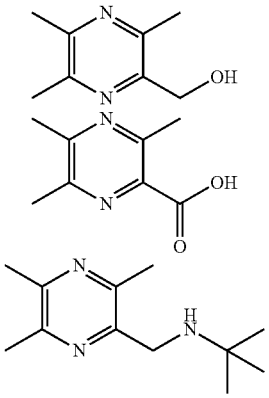

In additional embodiments, a method of preparation of the pyrazine derivative includes the steps of reacting 3,6-dimethyl-2,5-pyrazine dicarboxaldehyde with tert-butyl hydroxylamine; or reacting 3,6-dimethyl-2,5-dibromo methylpyrazine with tert-butyl hydroxylamine, and then oxidizing with sodium tungstate and hydrogen peroxide.

The novel compounds as described herein include compositions of pyrazine derivatives with nitrones and pyrazine derivative with other biologically active moieties, both of the compositions are antioxidants with antithrombotic activity. On one hand, these compounds are able to eliminate the radicals in the blood and tissues of human body including superoxide anion ($O_2.^-$), peroxynitrite nitrate ($ONOO^-$) and hydroxyl radical (.OH); and on the other hand, these compounds are able to dissolve thrombus in blood vessels. Therefore, these compounds can be used for treating and/or preventing the diseases caused by excessive production of free radicals and/or thrombosis. These diseases include but not limited to nervous system diseases, such as hypoxic-ischemic herebral damage, stroke, cerebral trauma, Alzheimer's disease, epilepsy, Parkinson disease, Huntington's disease, amyotrophic lateral sclerosis, AIDS dementia, multiple sclerosis, chronic pain, priapism, cystic fibrosis, schizophrenia, depression, premenstrual syndrome, anxiety, addiction, and migraines; also include cardiovascular diseases, such as cardiopulmonary lateral flow, respiratory distress syndrome, heart ischemia-reperfusion, heart ischemia-reperfusion, toxic shock syndrome, adult respiratory distress syndrome, cachexia, myocarditis, atherosclerosis, coronary heart disease, and heart attack; also include inflammatory infectious diseases, such as inflammatory bowel disease, diabetes mellitus, rheumatoid arthritis, asthma, hepatic cirrhosis, allograft rejection, encephalomyelitis, meningitis, pancreatitis, peritonitis, vasculitis, lymphocytic choriomeningitis, glomerulonephritis, systemic lupus erythematosus, stomach bowel disorders, obesity, hunger disease, hepatitis, and renal failure; also include eye disorders, such as diabetic retinopathy, uveitis, glaucoma, blepharitis, chalazion, allergic ocular disease, corneal ulcers, keratitis, cataract, senile macular degeneration, and optic neuritis; and further these compounds can be used for treating and/or preventing cancers, such as neuroblastoma.

The embodiments of the invention provide compositions of pyrazine derivatives with nitrons and pyrazine derivatives with biologically active moieties, and these compositions can be used to patients in the form of a pharmaceutical acceptable salts or complex drugs. A certain component needs to be mixed with an appropriate carrier or excipient to form a pharmaceutical composition to reach a desirable therapeutically effective amount. "Therapeutically effective amount" is intended to include a necessary amount of a compound described herein, or of a combination of compounds described herein when the compound or the combination of the compounds are used to attain a therapeutic effect for treating and/or preventing a disease, such as the effects of restraining excessive amount of radicals, and mitigating cell damages caused by stroke, heart attack or infectious disease.

The compounds as described herein can be prepared in different dosage forms, which include solid, semi-solid, liquid, and aerosol (*Remington's Pharmaceutical Sciences*, Mack. Publishing Company (1995), Philadelphia, Pa., 19$^{th}$ ed). These dosage forms can be further divided into more specific forms, including tablet, pill, sugar lozenge, granule, gel, paste, solution, suppository, injection, inhalant and spray. These dosage forms can be used for local or systemic administration and for immediate-release or sustained release. There are many routes of administration of these drugs, which include oral, buccal, rectal, peritoneal, intraperitoneal, transdermal administration, subcutaneous and endotracheal administrations.

When the compound or composition as described herein is applied in a dosage form of injection, the compound or composition can be prepared, by using a water-soluble or lipid-soluble solvent, into a solution, suspension or emulsion. The lipid-soluble solvent can be, for example, plant oil, synthetic fatty acid glyceride, higher fatty acid ester and/or proylene glycol. The compounds as described herein are more readily dissolved in Hank's solution, Ringer's solution or physiological saline.

When applied through oral administration, the compound or composition as described herein can be prepared through certain common techniques into a complex by adding a pharmaceutical acceptable excipient. Such excipients can be used to prepare these compounds into different dosage forms, such as tablet, pill, suspension, and gel. There are many ways for oral preparation, for example, by mixing the compound and the solid excipient, grinding fully the resulting mixture, adding appropriate auxiliary agents, and processing the mixture into particles. The auxiliary agents, which can be used for oral preparation, include, for example, sugars such as lactose, sucrose, mannitol, or sorbitol; celluloses such as corn starch, wheat starch, potato starch, gelatin, gummi tragacanthae, methyl cellulose, hydroxyproylmethyl-cellulose, sodium carboxymethyl cellulose, and polyethylene pyrrole ketones.

The compounds as described herein can be prepared also in the form of spray, which can be achieved by using a pressurizer and a sprayer or dry powder inhaling device. Suitable spray agents used for spraying include, for example, dichlorodifluoromethane, fluorine chloroform, dichloro-tetrafluoroethane, carbon dioxide, and dimethyl ether. The amount of spray delivered from a sprayer can be controlled by the adjustment of the injecting valve of the sprayer.

The dosage forms as described herein are all related to the therapeutically effective amount of the compounds of the invention. The therapeutically effective amount of the compounds as described herein may depend on specific conditions of patients under the treatment. To determine the appropriate dose, various factors much be taken into account, for example, the route of administration to be used, weight and conditions of the patient to be treated, and observation and subjective judgment made by the prescribing physician. The therapeutically effective amount is usually determined by an experienced prescribing physician.

EXAMPLES

The following examples are intended for illustration only and are not intended to limit the scope of the invention in any way.

Example 1

Synthesis of TN-2 (FIG. 1)

In a 500 mL three-necked flask was placed methanol (200 mL), and 3,6-dimethyl-2,5-pyrazine dicarboxaldehyde (2.0 g, 0.012 mol) was added, then tert-butyl hydroxylamine (4.3 g, 0.048 mol) was added, and the reaction was heated under reflux for 3 hrs. The obtained mixture was separated by column chromatography (ethyl acetate 100%) to obtain a light yellow solid compound TN-2 (1.0 g). Yield: 26.8%, mp: 198-201° C. $^1$HNMR (CDCl$_3$): 1.61 (s, 18H), 2.48 (s, 3H), 2.50 (s, 3H), 7.83 (s, 2H); ESI-MS: 307 [M+H]$^+$, 329 [M+Na]$^+$; Anal. (C$_{12}$H$_{19}$N$_3$O) C. H. N. found C 62.52%, H 8.73%, N 18.19%; requires: C, 65.13; H, 8.65; N, 18.99.

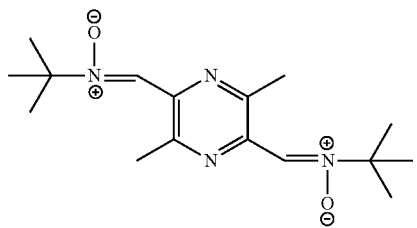

TN-2

Example 2

Figure 2:
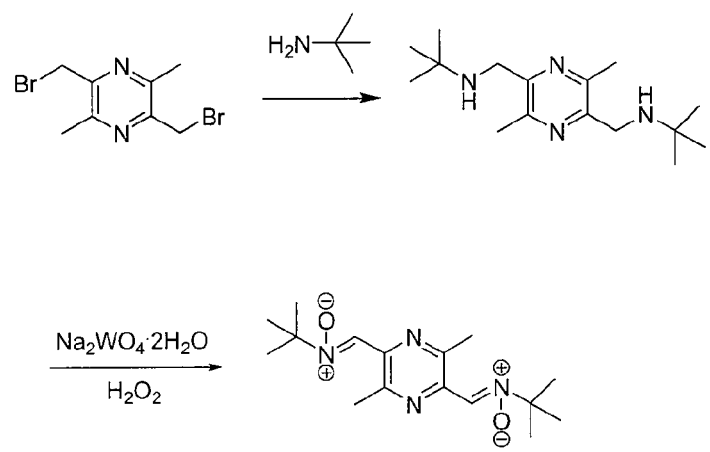
FIG. 2 illustrates a synthetic process for the compound TN-2 according to another embodiment of the present invention.

Synthesis of TN-2 (FIG. 2)

In a 250 mL round-bottomed flask was placed 2,5-di-tert-butylamine methyl-3,6-dimethyl pyrazine (5.6 g, 0.02 mol) was added, an appropriate amount of methanol was added, then Na$_2$WO$_4$.2H$_2$O (1.64 g, 0.005 mol) and 30% H$_2$O$_2$ (10 mL) were added, and the reaction was stirred at room temperature for 2 hrs. The resultant mixture was filtered and evaporated to remove methanol, saturated Na$_2$S$_2$O$_3$ was added, extracted with ethyl acetate, evaporated to remove most of the ethyl acetate. The product was separated by using column chromatography (ethyl acetate, 100%) to obtain a white solid TN-2 (1.97 g), in a yield of 32%. The analytical data are the same as above in Example 1.

Example 3

Synthesis of TN-4

In a 250 mL three-necked flask was added 2-methyl-quinoxaline (2.88 g, 0.02 mol), benzoyl peroxide (20 mg) was added, $CCl_4$ (80 mL) was added, and the reaction was refluxed at 70° C. for 10 hrs. The reaction was cooled and then filtered to obtain a crude 2-bromomethyl quinoxaline, the compound obtained was not separated and to the resulting material was added an excess amount of tert-butyl amine, and the reaction was stirred at room temperature for 3 hrs to obtain 5-methyl tert-butylamine quinoxaline (1.25 mg), in a yield of 29.1%.

To the above-obtained compound (670 mg, 0.006 mol) were added methanol (60 mL), $Na_2WO_4 \cdot 2H_2O$ (0.18 g) and 30% $H_2O_2$ (1.75 mL), the reaction was run at room temperature for 2.5 hrs. The product was separated by column chromatography (ethyl acetate:petroleum ether=4:1) to obtain a light yellow compound TN-3 (460 mg) in a yield of 35.9%. $^1$HNMR ($CDCl_3$): 1.70 (s, 9H), 7.77 (m, 2H), 8.03 (m, 2H), 8.14 (s, 1H), 10.49 (s, 1H); ESI-MS: 230 $[M+H]^+$; Anal. ($C_{13}H_{15}N_3O$) C. H. N. found C 67.80%, H 6.90%, N 17.86%; requires: C, 68.10; H, 6.59; N, 18.33.

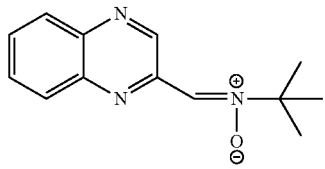

TN-4

Example 4

Synthesis of TN-5

In a 250 mL three-necked bottle was placed 5-methyl quinoxaline (2.88 g, 0.02 mol), benzoyl peroxide (20 mg) was added, $CCl_4$ (80 mL) was added, then the reaction was refluxed at 70° C. for 10 hrs. The product was cooled and filtered to obtain a crude 2-bromomethyl quinoxaline, the compound was not separated, an excess amount of tert-butyl amine was added, and the reaction was stirred at room temperature for 3 hrs to obtain 5-methyl tert-butylamine quinoxaline (670 mg) in a yield of 15.6%.

The above-obtained compound (670 mg, 0.003 mol) were added methanol (60 mL), $Na_2WO_4 \cdot 2H_2O$ (0.1 g) and 30% $H_2O_2$ (3.5 mL), the reaction was proceeded at room temperature for 2.5 hrs. The product was separated by column chromatography (ethyl acetate:petroleum ether=2:1) to obtain a light yellow compound TN-4 (154 mg) in a yield of 21.5%. $^1$HNMR ($CDCl_3$): 1.69 (s, 9H), 7.83 (dd, 1H), 8.10 (dd, 1H), 8.80 (d, 1H), 8.87 (d, 1H), 9.19 (s, 1H), 9.96 (dd, 1H); ESI-MS: 230 $[M+H]^+$; Anal. ($C_{13}H_{15}N_3O$) C. H. N. found C 68.04%, H 6.95%, N 18.0%; requires: C, 68.10; H, 6.59; N, 18.33.

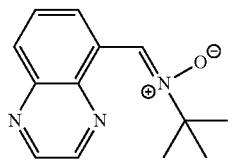

TN-5

Example 5

Synthesis of TN-6

In a 250 mL three-necked bottle was placed 3,5,6-trimethyl-2-bromide methylpyrazine (4.28 g, 0.02 mol), then an appropriate amount of tert-butyl amine was added dropwise, and the reaction was stirred at room temperature for 12 hrs, filtered and evaporated to dryness, the crude product was separated by column chromatography (petroleum ether:ethyl acetate=5:1) to obtain a white powder solid (1.57 g), in a yield of 25%. $^1$HNMR ($CDCl_3$): 1.25 (s, 9H), 2.30 (s, 6H), 2.35 (s, 6H), 2.39 (s, 6H), 3.86 (s, 4H); ESI-MS: 342 $[M+H]^+$, 364 $[M+Na]^+$; Anal. ($C_{12}H_{19}N_3O$) C. H. N. found C 62.52%, H 8.73%, N 18.19%; requires: C, 65.13; H, 8.65; N, 18.99.

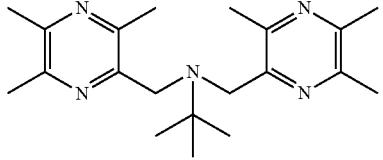

TN-6

Example 6

Synthesis of TN-7

To the compound TN-6 (0.682 g, 0.002 mol) obtained in Example 5 was added 1,4-dioxane (100 mL), then an active selenium dioxide (330 mg, 0.003 mol) was added, the reaction was heated under reflux at 107° C. for 3 hrs, a light yellow color was indicated by using 2,4-dinitrophenylhydrazine. The product was cooled to room temperature, evaporated to remove 1,4-dioxane, and separated by column chromatography (petroleum ether:ethyl acetate=2:1) to obtain a solid (237.8 mg) in a yield of 33.5%.

To ethanol (100 mL) was added the above-obtained solid (237.8 mg) was added, and then tert-butyl hydroxylamine (0.12 g) was added. The reaction was refluxed at 84° C. for 3 hrs, then cooled to room temperature, and evaporated to remove ethanol. The product was separated by column chromatography (petroleum ether:ethyl acetate=5:1) to obtain a light yellow solid (183.5 mg), in a yield of 64.3%. ESI-MS: 427 $[M+H]^+$, 449 $[M+Na]^+$.

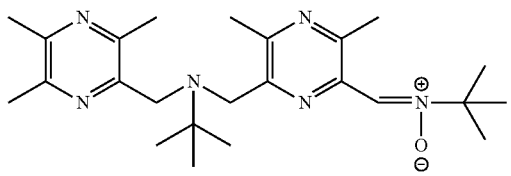

TN-7

Example 7

Synthesis of TN-15

In an appropriate amount of THF was dissolved 2-hydroxymethyl-3,5,6-trimethyl pyrazine (3.04 g, 0.02 mol), NaOH (2 g, 0.05 mol) was added, and then 3,5,6-trimethyl-2-bromide methylpyrazine (5.35 g, 0.025 mol) was added at stirring at room temperature. The product was filtered and the filtrate evaporated to dryness, the resultant crude material was separated by column chromatography (petroleum ether:ethyl acetate=3:1) to obtain a white powder solid (4.8 g), in a yield of 84%. ESI-MS: 287 [M+H]$^+$, 309 [M+Na]$^+$.

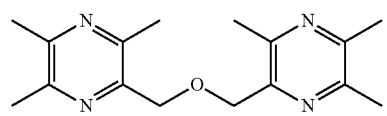

TN-15

Example 8

Synthesis of TN-16

In an appropriate amount of THF was dissolved 2-formic acid-3,5,6-trimethyl pyrazine (3.32 g, 0.02 mol), then K$_2$CO$_3$ (6.90 g, 0.05 mol) was added, and 3,5,6-trimethyl-2-bromide methylpyrazine (5.35 g, 0.025 mol) was added at stirring at room temperature. The product was filtered and the filtrate was evaporated to dryness, and the resultant crude material was separated by column chromatography (petroleum ether: ethyl acetate=3:1) to obtain a white powder solid (4.5 g) in a yield of 75%. ESI-MS: 301 [M+H]$^+$, 323 [M+Na]$^+$.

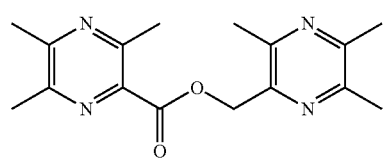

TN-16

Example 9

Synthesis of TN-17

Biotin (4.88 g, 0.02 mol) was dissolved in DMF (100 mL). Triethylamine (2.9 mL, 0.02 mol) and 3,5,6-trimethyl-2-bromide methylpyrazine (5.35 g, 0.025 mol) were added dropwise at stirring. The reaction was stirred at room temperature for 5 hrs. The completion of the reaction was detected by TLC. Water (80 mL) was added for dilution, and the mixture was extracted with chloroform (100 mL×2), the combined organic phases were washed with water (100 mL×2), dried with anhydrous Na$_2$SO$_4$. The product was separated by column chromatography to obtain a white powder solid (5.2 g), in a yield of 68.8%. ESI-MS: 379 [M+H]$^+$, 401 [M+Na]$^+$.

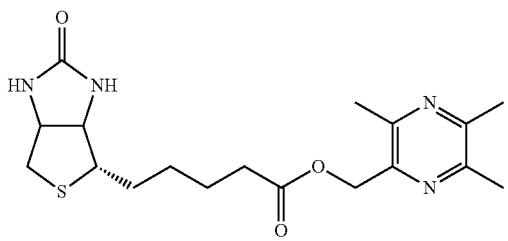

TN-17

Example 10

Figure 3:
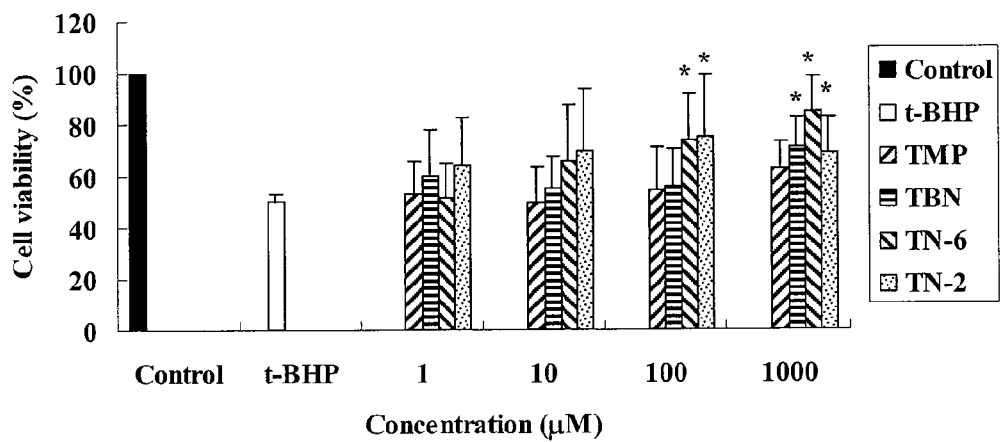
FIG. 3 shows that the compound TN-2 has significant protective effects for PC12 cells induced by tert-butyl hydroperoxide (t-BHP).

Tests on Cytoprotection of Brain Cells of Rats by Using TBN (FIG. 3)

PC12 cells were inoculated in a 96-well plate of strong adsorption with 90 μL per well, cultured for 36 hrs in an incubator set at 37° C. and 5% CO$_2$. After 36 hrs, each of the drugs was added in four concentration gradients. Cultured for half an hour in an incubator set at 37° C. and 5% CO$_2$, replaced with serum-free medium, t-BHP (10 mL, final concentration of 200 μM) was added in each of the wells except the well of the control. Then the material was placed and cultured in an incubator for 24 hrs. The cells were cultured for 24 hrs, and MTT (15 μL, 5 mg/mL) was added in each of the wells. The material was cultured in an incubator for 4 hrs, and then DMSO (150 mL) was added in each of the wells to be further incubated for at least half an hour to ensure the crystals were completely dissolved. The absorbance (A value) was measured by using a micro-plate reader at 570 nm. The results showed significant effect of cytoprotection of TN-2 towards the t-BHP-induced cell damage; the intensity of the effect was significantly higher than that of TMP, (FIG. 3). As shown in FIG. 3, *P<0.05 as compared with the t-BHP group; the difference is significant.

Example 11

Figure 4:
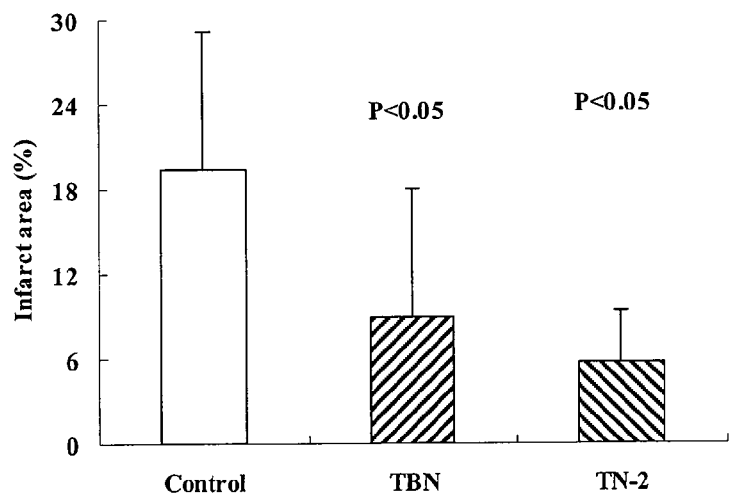
FIG. 4 shows the protective effects of the compound TN-2 for the rats with ischemia caused by MCAo.

Tests on Cytoprotection of Rats Having Cerebral Ischemia Caused by MCAO by Using TN-2 (FIG. 4)

Anesthesia was performed on rats (female SD rats, in body weight of 260-300 g) with intraperitoneal injection of 10% hydrated chloral hydrate in a dose of 400 mg/kg or with inhalation of 3.5% halothane. At the entrance of MCAO (Middle Cerebral Artery Occlusion Ischemia) was blocked with a nylon wire to cause cerebral ischemia. After ischemia occurred for 1 hr, the rats were respectively intravenously injected with EDA (63 mg/kg), TBN (80 mg/kg), TN-2 (65 mg/kg), and saline (control group). There were 6 rats in each group. After ischemia occurred for 2 hrs, the nylon wires were removed, and reperfusion was performed for 24 hrs. Brain tissues were taken and the cerebellums were removed. The material was rinsed in PBS solution, and put in a freezer set at −20° C. for a moment, and the brain tissues were cut into slices with a thickness of about 2 mm, and immediately placed in a solution of 0.5% triphenyltetrazolium chloride (TTC). Incubation was performed at 37° C. for 30 minutes. The extent of cerebral infarction was evaluated. The results showed significant treatment effects of TN-2 on stroke of the rats (FIG. 4). In FIG. 4, the data were examined by one-tailed t-test; the mark "*" refers to the data in comparison with the control; drug dosage: TBN (80 mg/kg), and Edaravone (63 mg/kg); and each of the drugs were used in equal molarity.

Example 12

Tests on Cytoprotection on Injuries of Dopaminergic Neuronsinduced by MPP+ using TN-2 (FIG. 6)

Figure 5:
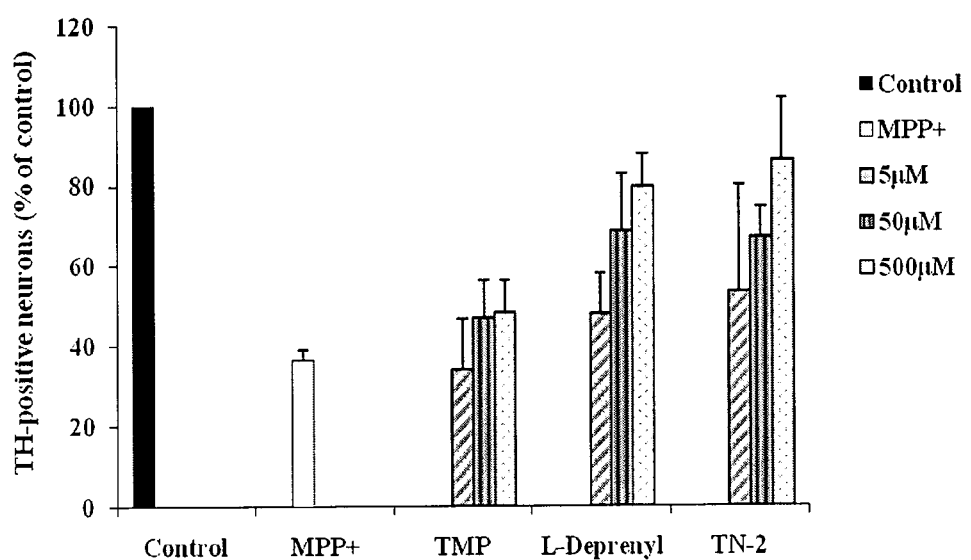
FIG. 5 shows the protective effects of the compound TN-2 for the damage of dopaminergic neuron induced by $MPP^+$.

Dopaminergic neurons were cultured for 5 days, and L-Deprenyl, TMP and TN-2 were added in a concentration gradient of 500 μM, 50 μM and 5 μM respectively. Two hours later, MPP+(with a final concentration of 10 μM) was added into each of the wells except those of the control. As shown in FIG. 5, the results indicated that the effects of cytoprotection by TN-2 to the MPP+-induced cell damage were significant.

In the foregoing description of the embodiments, it is indicated that the present invention, through the novel compounds and their uses described herein, provided useful and unique approaches for the treatment or prevention of the diseases, such as neurological disorder, cardiovascular disease, inflammation and cancer, caused by excess amount of radicals. While certain specific embodiments have been described in detail, many details have been set forth for purposes of illustration and are not intended to limit the scope of the claims attached hereafter. It should be understood that the invention is susceptible to additional embodiments and that certain of the details described herein may be varied considerably with different substitutions, changes and modifications without deviating from the basic principles of the invention defined by the claims attached herein and their equivalents.

The invention claimed is:

1. A pyrazine derivative of formula I

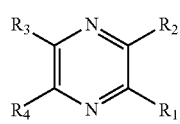

I or a pharmaceutical acceptable thereof, wherein:
$R_1$ and $R_3$ are each independently a nitronyl group, such that the pyrazine derivative has a structure of formula II:

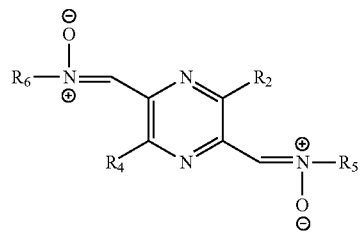

II wherein $R_5$ and $R_6$ are each independently a substituted or unsubstituted straight-chain alkyl, branched-chain alkyl, or cycloalkyl;
$R_2$ and $R_4$ are each independently hydrogen, hydroxyl, or a substituted or unsubstituted group selected from amino, carboxyl, alkyl, alkoxy, aryl, heteroaryl, and nitronyl group.

2. The pyrazine derivative according to claim 1, wherein $R_2$ and $R_4$ are alkyl.

3. The pyrazine derivative according to claim 2, wherein $R_2$ and $R_4$ are methyl, $R_5$ and $R_6$ are tert-butyl, the pyrazine derivative having a structure of TN-2:

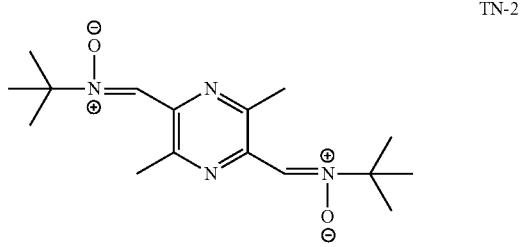 [SMILES: Cc1nc(/C=[N+](/[O-])C(C)(C)C)c(C)nc1/C=[N+](/[O-])C(C)(C)C]

TN-2

4. The pyrazine derivative according to claim 2, wherein $R_2$ and $R_4$ are methyl, $R_5$ and $R_6$ are cyclohexyl, the pyrazine derivative having a structure of TN-3:

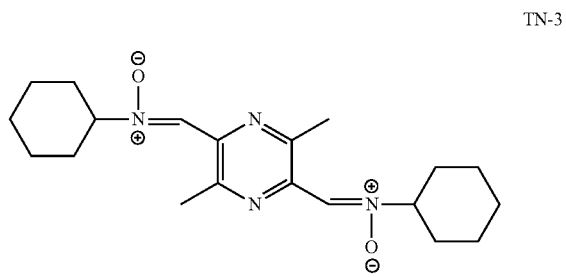 [SMILES: Cc1nc(/C=[N+](/[O-])C2CCCCC2)c(C)nc1/C=[N+](/[O-])C1CCCCC1]

TN-3

5. A pharmaceutical composition, comprising the pyrazine derivative of claim 1 as a pharmaceutical active ingredient in a therapeutically effective amount, and a pharmaceutically acceptable carrier and excipient.

* * * * *

UNITED STATES PATENT AND TRADEMARK OFFICE
CERTIFICATE OF CORRECTION

PATENT NO. : 8,796,281 B2  
APPLICATION NO. : 13/254653  
DATED : August 5, 2014  
INVENTOR(S) : Wang et al.

It is certified that error appears in the above-identified patent and that said Letters Patent is hereby corrected as shown below:

On the Title page, in item (54) and in the Specification, in column 1, line 1-2, in "Title", delete "LIGHTING DEVICE HAVING AT LEAST ONE HEAT SINK" and insert --PYRAZINE DERIVATIVES, PROCESS FOR MANUFACTURE AND USE THEREOF--, therefor On the Title page, in column 2, item (56) under "Other Publications", line 6, delete "Pyrazylethanoi" and insert --Pyrazylethanol--, therefor Signed and Sealed this  
Twenty-fifth Day of November, 2014

Michelle K. Lee  
*Deputy Director of the United States Patent and Trademark Office*